US00PP25947P3

(12) United States Plant Patent
Olesen

(10) Patent No.: US PP25,947 P3
(45) Date of Patent: Sep. 29, 2015

(54) MINIATURE ROSE PLANT NAMED 'POULPAR081'

(50) Latin Name: ***Rosa* hybrid**
Varietal Denomination: Poulpar081

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 189 days.

(21) Appl. No.: 13/986,935

(22) Filed: Jun. 14, 2013

(65) Prior Publication Data

US 2014/0373218 P1 Dec. 18, 2014

(51) Int. Cl.
*A01H 5/02* (2006.01)

(52) U.S. Cl.
USPC ..... Plt./121

(58) Field of Classification Search
USPC ..... Plt./121
See application file for complete search history.

(56) References Cited

PUBLICATIONS

UPOV—Pluto Plant Variety Database International Union for the Protection of New Varieties of Plants, Jan. 19, 2015, obtained for cultivar name 'Poulpar081' (1 page total).*
Poulsen Roser A/S catalog; Retrieved from the Internet http://www.poulsenroser.com (1 page total).*

* cited by examiner

*Primary Examiner* — Susan McCormick Ewoldt

(57) ABSTRACT

A new miniature rose plant that has abundant, pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar081'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpar081', originated as a single seedling from the stated cross.

The new variety may be distinguished from its male pollen parent and female seed parent primarily by flower coloration and growth habit. The male pollen parent has apricot colored flowers while the new variety has light pink flowers. The female seed parent is 25 to 30 cm in height, while the claimed variety is 20 cm in height.

The objective of the hybridization of this rose variety for commercial culture was to create a new and distinct variety with unique qualities, such as:

1. Uniform and abundant pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar081' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar081' was selected by the inventor as a single plant from the progeny of the hybridization in 2007.

Asexual reproduction of 'Poulpar081' by cuttings was first done by Mogens N. Olesen in the nursery in Fredensborg, Denmark in 2008. This initial and other subsequent propagations conducted in controlled environments have demonstrated that the characteristics of 'Poulpar081' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar081'.

Specifically illustrated in the drawing are flowers at various stages of development, flower in parts, leaves, and stems. Illustrated plants are 3 months of age.

DETAILED DESCRIPTION OF THE VARIETY

The following is a description of 'Poulpar081', as observed in its growth in glasshouses in Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulhi008', U.S. Plant Pat. No. 15,722 are compared to 'Poulpar081' in Chart 1.

CHART 1

| | 'Poulpar081' | 'Poulhi008' |
|---|---|---|
| Petalage: | 30 petals total, 5 of which are petaloids | 40-45 |
| Flower Diameter: | 55 mm | 80 mm |
| General Tonality of Flower Color: | Red-Purple Group 65D with light intonations of Red Group 55C | Red Group 55B |

Flower and Flower Bud

Blooming habit: Continuous.

Flower bud:

*Size.*—Upon opening, 21 mm in length from base of receptacle to end of bud. 14 mm in diameter.

*Bud form.*—

*Bud color.*—As sepals unfold, petals are Red-Purple Group 62D with intonations of Red Group 38C.

*Sepals.*—Upper Surface: Color: Generally Green Group 138B. Apex is Green Group 137B with intonations of Greyed-Red Group 178A on some of the sepals. Texture: Smooth, moderately pubescent. Lower Surface: Color: Yellow Green Group 144A. The apex is occasionally Greyed-Red Group 178A. Texture: Smooth. Shape: Apex: Cirrhose. Base: Flat at union with receptacle. Margins: Margins have strong to very strong foliaceous appendages on three of the five sepals. Size: 35 mm long by 7 mm wide.

*Receptacle.*—Surface Texture: Smooth. Shape: Funnel shaped. Size: 10-15 mm tall and 8 mm wide. Color: Yellow Green Group 144A.

*Pedicel.*—Surface: Smooth. Length: 30 mm on average. Diameter: Generally 2.5 mm. Color: Yellow-Green Group 144A. Strength: Medium strength.

*Borne.*—Singly.

Flower bloom:

*Fragrance.*—Medium floral scent.

*Duration.*—As a pot plant, flowers last up to 28 days.

*Size.*—On average flower diameter is 55 mm, depth is 30 mm.

*Form.*—General shape is a hybrid tea with a high pointed center.

*Shape of flower, side view.*—The upper portion is flat. The lower portion is a concave.

Petalage: On average, flowers have 30 petals total, 5 of which are petaloids.

Color:

*General tonality.*—On open flower Red-Purple Group 65D with light intonations of Red Group 55C.

*Upon opening, petals.*—Outermost petals are White Group 155B with intonations of Red-Purple Group 65D on the upper surface. White Group 155B shaded with Red-Purple Group 62C on the lower surface. Innermost petals are White Group 155B with intonations of Red-Purple Group 65D on the upper surface. White Group 155B shaded with Red-Purple Group 62C and Red Group 58D on the lower surface.

*After opening, petals.*—Outermost petals are Red-Purple Group 69A on the upper surface. Red-Purple Group 65C on the lower surface. Innermost petals are Red-Purple Group 69A on the upper surface. Red-Purple Group 65D with intonations of Red-Purple Group 65A on the lower surface. At the base of the petal, the upper and under surface are Green-White Group 157A.

Petals:

*Petal reflex.*—Strong.

*Margin.*—Entire, moderate undulations.

*Shape.*—Generally ovate. Apex shape: Rounded. Base shape: Obtuse.

*Size.*—35 mm (l) by 40 mm (w).

*Texture.*—Smooth.

*Thickness.*—Average.

Petaloids:

Quantity.—5 on average.

*Shape.*—The apex is rounded and the base is acute. Petaloids are ruffled.

*Color.*—White Group 155A with intonations of Red-Purple Group 65B on upper and undersurface.

*Size.*—15 mm (l) by 18 mm (w).

Reproductive organs:

*Pollen.*—None Observed.

*Anthers.*—Size: 1.5 mm long. Color: Greyed-Orange Group 164B. Quantity: 40 to 45.

*Filaments.*—Color: Yellow Group 4D. Length: About 5 mm.

*Pistils.*—Length: About 3 mm long. Quantity: 30 on average.

*Stigmas.*—Color: Greyed-Yellow Group 161B.

*Styles.*—Color: Red Group 47B.

*Seed formation.*—Not observed.

Plant

Plant growth: Upright. Plants are 20 cm in height, and 15 cm wide.

Stems:

*Color.*—Juvenile growth: Yellow-Green Group 144A with occasional intonations of Greyed-Orange Group 175A. Mature growth: Yellow-Green Group 146A.

*Length.*—Canes are 11 cm from the base of the plant to the flowering portion.

*Diameter.*—3 mm.

*Internodes.*—On mature canes, there is an average distance of 20 mm between nodes.

*Surface texture.*—Young and mature wood is smooth.

Prickles:

*Incidence.*—3 per 10 cm of stem.

*Size.*—5 mm long.

*Color.*—Greyed-Purple Group 185B on mature and juvenile prickles.

*Shape.*—Linear to deep concave.

Plant foliage:

*Compound leaf size.*—70 mm (l) by 50 mm (w).

*Quantity.*—4 leaves per 10 cm of stem.

*Leaf bearing angle to the stem.*—60 degrees.

*Color of juvenile foliage.*—Upper Leaf Surface: Yellow-Green Group 146C with margins Greyed-Red Group 181A. Lower Leaf Surface: Yellow-Green Group 146D shaded with Greyed-Red Group 181B.

*Color of mature foliage*.—Upper Leaf Surface: Yellow-Green Group 147A. On some margins anthocyanin the color of Greyed-Purple Group 185A. Lower Leaf Surface: Green Group 138B.

Plant leaves and leaflets:

*Stipules*.—Size: About 6 mm in length. Shape: Linear, slightly broad based with outward extending apecies. Margins: Finely serrated with few stipitate glands. Color: Yellow-Green Group 144A.

*Petiole*.—Length: 11 mm on average. Diameter: About 1 mm. Upper surface: Yellow-Green Group 144A with anthocanin the color of Greyed-Purple Group 183B. Lower surface: Yellow-Green Group 144B.

*Rachis*.—Length: 18 mm on average. Diameter: About 1 mm. Upper surface: Yellow-Green Group 144A with anthocanin the color of Greyed-Purple Group 183B. Lower surface: Yellow-Green Group 144B. Small prickles.

*Leaflet*.—Number of leaflets: 5 on normal leaves in middle of the stem. Size: 30 mm in length by 20 mm wide. Margin: Serrate. General Shape: Elliptical. Apex Shape: Acute. Base Shape: Round. Texture: Smooth. Arrangement: Odd pinnate. Venation: Reticulate. Leaf Gloss: Glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar081', substantially as illustrated and described herein, due to its abundant, pink flowers, vigorous growth, compact habit, suitability for production from softwood cuttings in pots, and durable flowers and foliage that make the variety suitable for distribution in the floral industry.

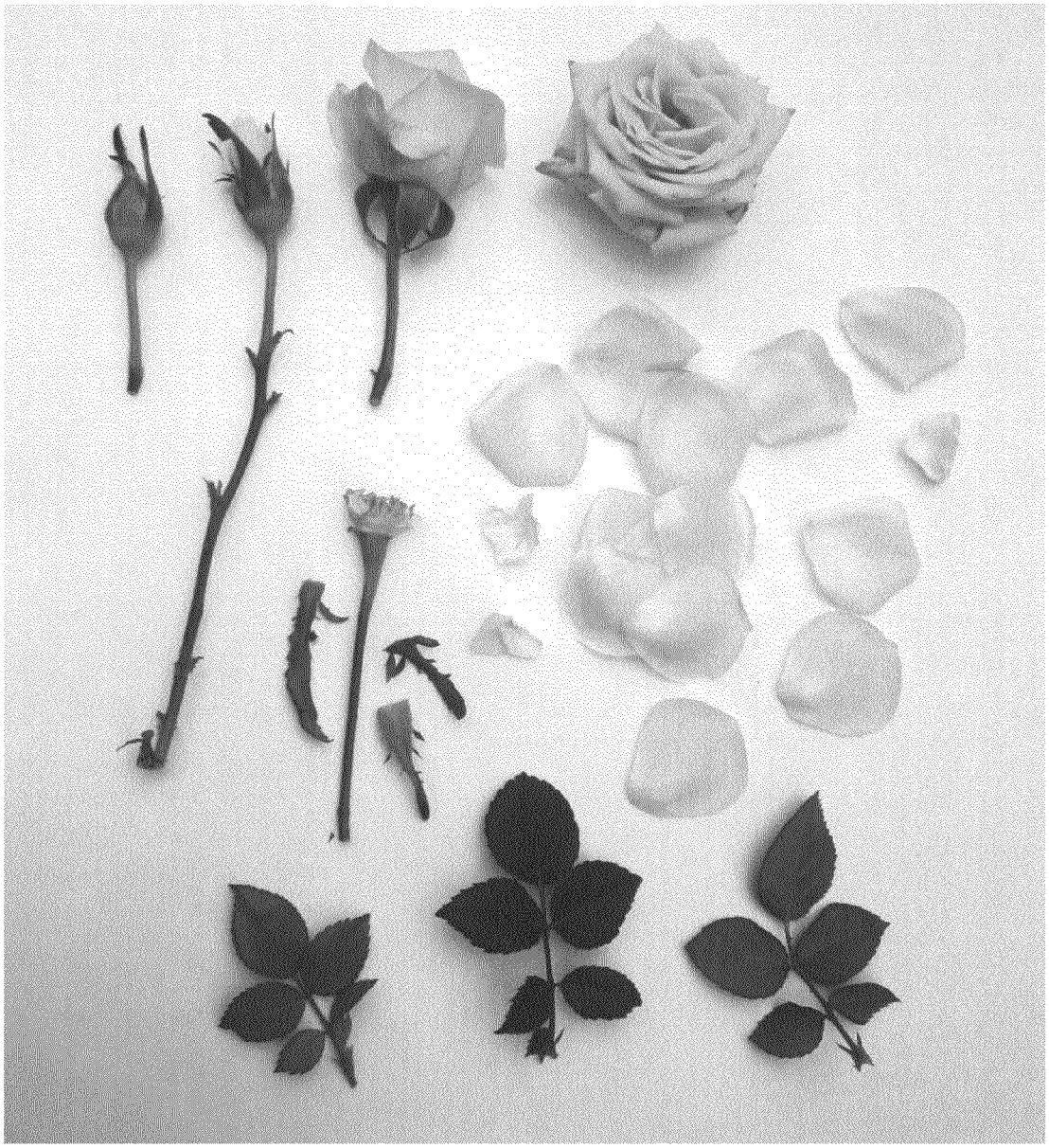

* * * * *